United States Patent

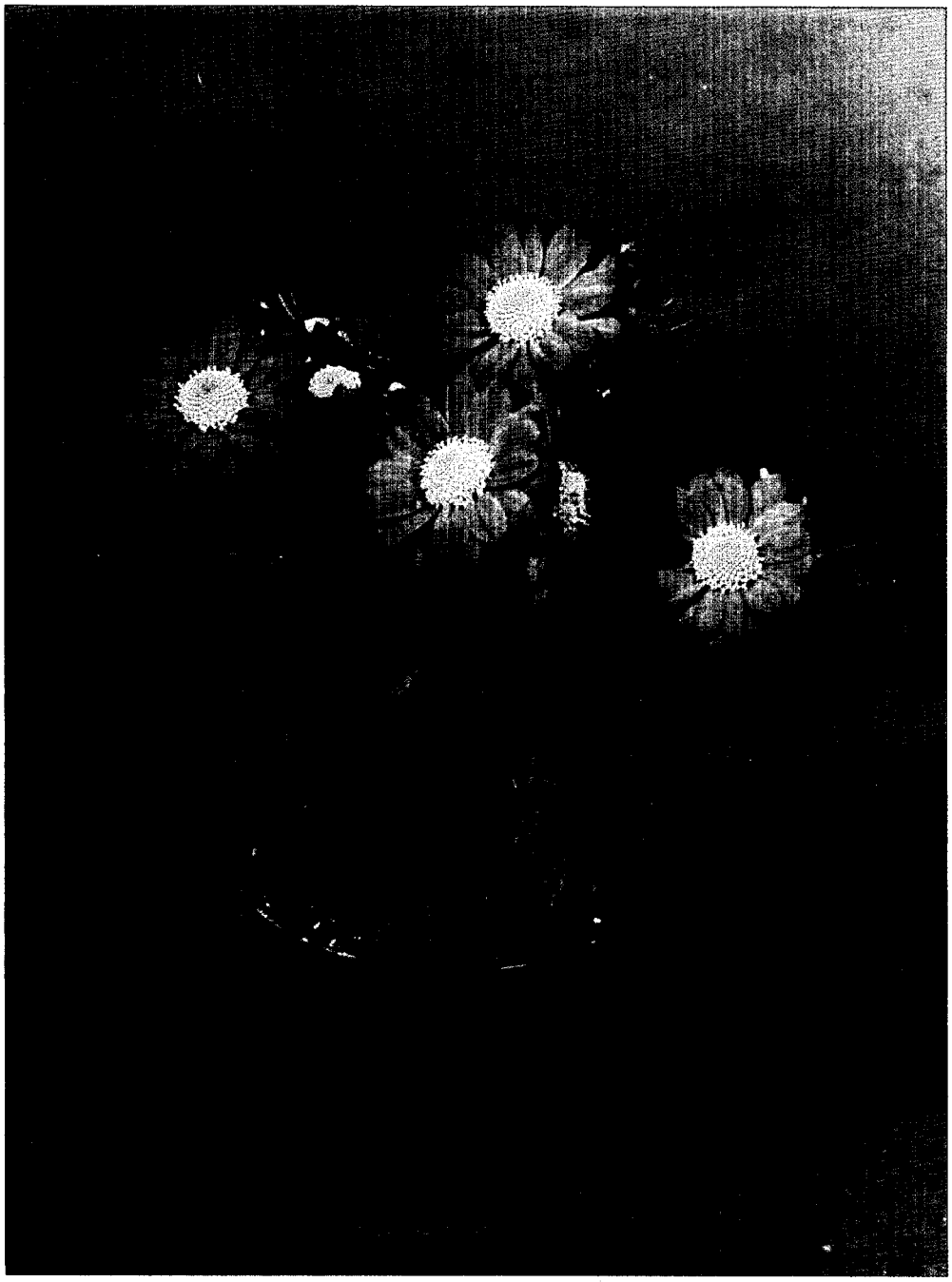

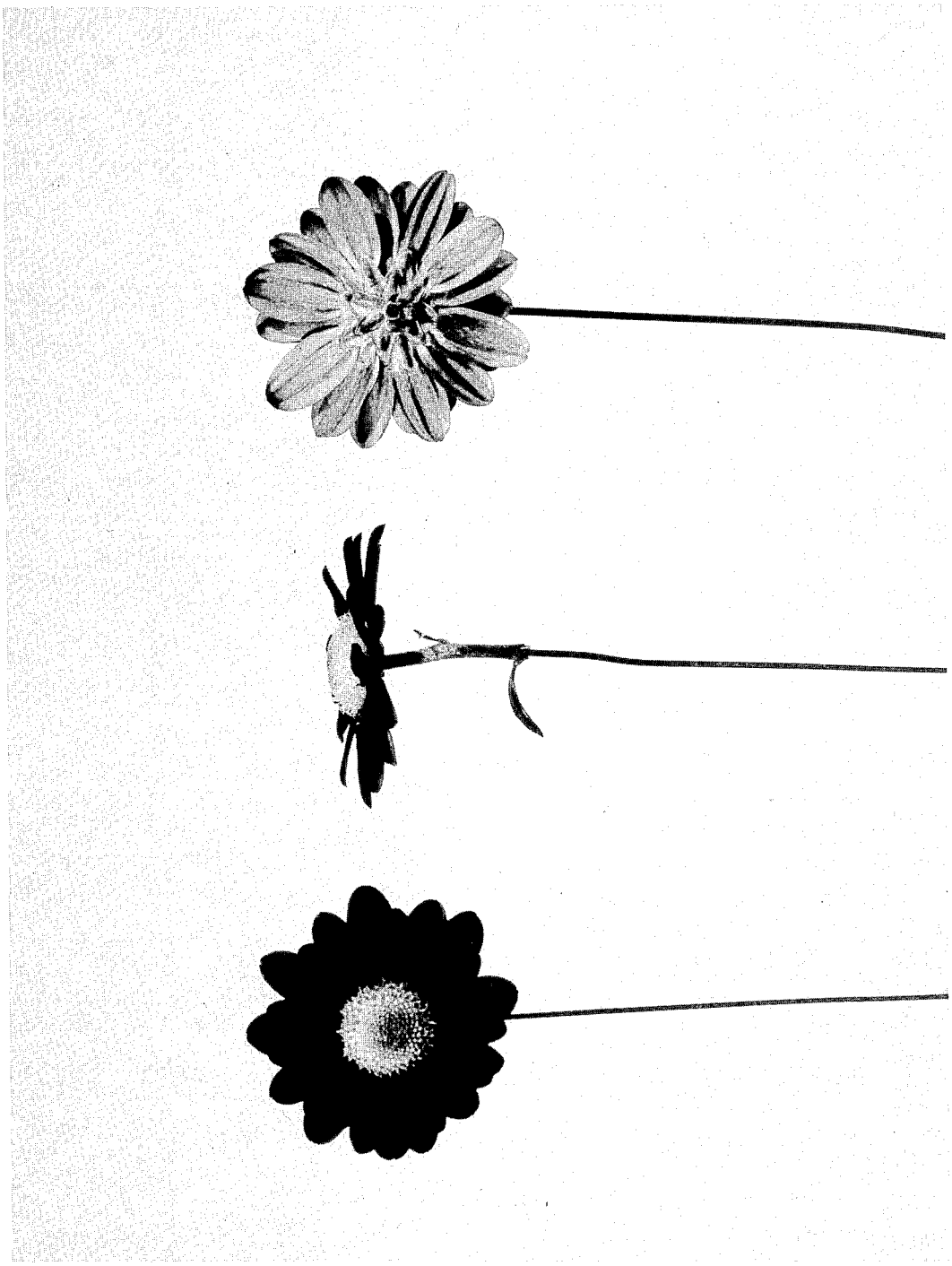

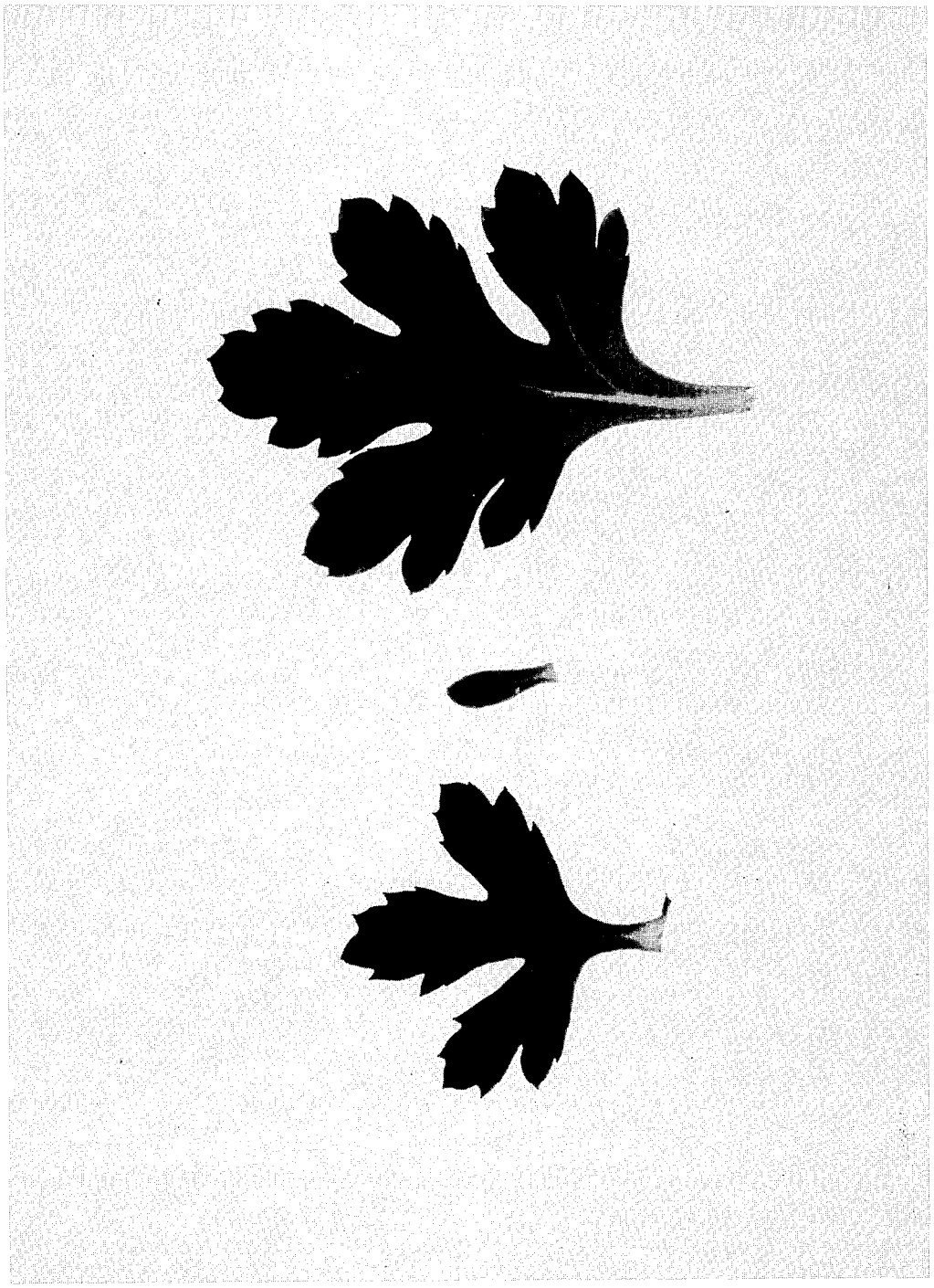

Plant Pat. 3,946

Patented Aug. 24, 1976

3,946

CHRYSANTHEMUM PLANT

Walter H. Jessel, Jr., Doylestown, and William E. Duffett, Akron, Ohio, assignors to Yoder Brothers, Inc., Barberton, Ohio

Filed July 24, 1975, Ser. No. 598,867

Int. Cl.[2] A01H *5/00*

U.S. Cl. Plt.—74 1 Claim

The present invention comprises a new and distinct cultivar of *Chrysanthemum morifolium,* Ramat., hereinafter referred to by the cultivar name Spark (#73156008).

Spark was originated from a cross made in a controlled breeding program in Barberton, Ohio in the year 1972. The female, or seed parent, was #71078021 (unnamed seedling), a red daisy originated by the present inventors from a cross between Dramatic (#67079001; U.S. Plant Pat. No. 3,189) and Mischief (#22019E01; unpatented; commercially available). The male, or pollen parent of Spark, was #71285002 (unnamed seedling), a yellow anemone originated by the present inventors from a cross between #70040020 (unnamed seedling) and #70010030 (unnamed seedling). Mischief is of parentage unknown to the present inventors. Dramatic, #70040020, and #70010030 are products of the breeding program of the present inventors.

Spark is a product of a planned breeding program which had the objective of creating cultivars readily adaptable for use in spray pot mum culture with daisy inflorescence type, intense red and red-bronze ray floret color, scarcity of pollen, spreading branching pattern, and with the ability to produce commercially acceptable quality in controlled flowering programs. These traits in combination were not present in previously available commercial cultivars.

Spark was discovered and selected as a flowering plant within the progeny of the stated cross by William E. Duffett and Walter H. Jessel, Jr. on Nov. 14, 1973 in a controlled environment in Barberton, Ohio.

The first act of asexual reproduction of Spark was accomplished when vegetative cuttings were taken from the initial selection in January 1974 in a controlled environment in Barberton, Ohio by a technician working under formulations established and supervised by William E. Duffett and Walter H. Jessel, Jr. Horticultural examination of selected units initiated May 17, 1974, has demonstrated that the combination of characteristics as herein disclosed for Spark are firmly fixed and are retained through successive generations of asexual reproduction.

Spark has not been observed under all possible environments. The phenotype may vary significantly with variations in environment such as temperature, light intensity, and daylength. The following observation, measurements, and comparisons describe plants grown in a greenhouse in Barberton, Ohio under environmental conditions which approximate those generally used in commercial practice, as described in Chart A and Chart B which appear at the end of the present specification.

The following traits have been repeatedly observed and are determined to be basic characteristics of Spark which in combination distinguish this chrysanthemum as a new and distinct cultivar:

(1) Flat influorescence form.
(2) Daisy inflorescence type. Slight elongation of disc florets produces crested anemone appearance.
(3) Red ray floret color.
(4) Semi-spreading branching pattern.
(5) Seven week flowering response.
(6) Medium plant height.
(7) Scant pollen.
(8) Permanence of inflorescence, averaging from 14 to 18 days.
(9) Dark green foliage color with high gloss appearance.

The accompanying photographic drawings show typical inflorescence and foliage characteristics of Spark with colors being as nearly true as possible with illustrations of this type. Sheet 1 is a color photograph of Spark. Sheet 2 is a black and white photograph showing three views of the inflorescence of Spark. Sheet 3 is a black and white photograph of the foliage of Spark at three stages of growth.

Of the many commercial cultivars known to the present inventors, the most similar existing cultivar is Fireside Cushion (#21680E06; unpatented). Reference is made to attached Chart C which compares certain characteristics of Fireside Cushion with the same characteristics of Spark. In comparison to Fireside Cushion, Spark has a more spreading branching pattern, less pollen and longer inflorescence permanence. The inflorescence form, inflorescence type, inflorescence color, and flowering response of Spark are similar to those of Fireside Cushion.

In the following description, color references are made to The Munsell Limit Color Cascade, 1972 edition. The color values were determined between 3:00 p.m. and 3:30 p.m. on May 5, 1975 under 150 foot candle light intensity.

BOTANICAL CLASSIFICATION

*Chrysanthemum morifolium,* Ramat., cv Spark.

I. Inflorescence

A. Capitulum:
*Form.*—Flat.
*Type.*—Daisy, with slight elongation of disc florets.
*Permanence.*—14 to 18 days.
*Diameter across face.*—1½ to 2¼ inches.

B. Corolla of ray florets:
*Texture (adaxial).*—Glabrous.
*Appearance and form.*—Ligulate.
*Arrangement.*—Whorled on receptacle.
*Persistence.*—Resists shatter.
*Color (abaxial).*—40–15 streaked with 40–14.

*Color* (*adaxial*).—Approximately 30–5 to 34–6 streaked with 40–12 to 40–15.

*Veination.*—Prominent.
*Margin.*—Moderately serrated.

CHART A—AVERAGE GREENHOUSE CHRYSANTHEMUM ENVIRONMENTS USED FOR BARBERTON, OHIO

| Season | Temperatures used (°F.) Night | Bright day | Cloudy day | Lighting used | Black cloth used | Supp., $CO_2$ |
|---|---|---|---|---|---|---|
| Fall | 65 to 56 | 65 to 80 | 60 to 75 | 2 to 4 weeks at 3 hours per night of 7–10 f.c. | To Sept. 15: on, 5:30 p.m.; off, 7:30 a.m. | From Oct. 15: 300 p.p.m. |
| Winter | 58 to 62 | 65 to 70 | 60 to 65 | 2 to 5 weeks at 5 hours per night of 7–10 f.c. | None | 300 p.p.m. |
| Spring | 58 to 65 | 65 to 80 | 60 to 75 | 2 to 4 weeks at 5 hours per night of 7–10 f.c. | From Mar. 15: on, 5:30 p.m.; off, 7:30 a.m. | To Apr. 15: 300 p.p.m. |
| Summer | 62 to 68 | 70 to 90 | 65 to 75 | 1 to 2 weeks at 3 hours per night of 7–10 f.c. | On, 6:00 p.m.; off, 8:00 a.m. | None. |

NOTE.—For intensity of direct solar radiation, refer to Chart B.

C. Corolla of disc florets:
*Appearance.*—Gameopetalous; tubular; slightly elongated; 5-lobed.
*Color.*—23–10 to 27–6.

D. Reproductive organs:
*Androecium.*—Present disc florets only; syngenesious Stamen; scant pollen.
*Gynoecium.*—Present both ray and disc florets; inferior, bicarpellate ovary; single style; 2-lobed stigma.

II. Plant

A. General appearance: Semi-spreading; medium height.
B. Duration and texture: Herbaceous; perennial.
C. Foliage:
*Color* (*abaxial*).—Approximately 21–13 to 21–16.
*Color* (*adaxial*).—21–13 overlaid with white.
*Shape.*—Spatulate; deeply lobed.
*Texture.*—Glabrous; leathery.
*Arrangement.*—Alternate.

CHART B

INTENSITY OF DIRECT SOLAR RADIATION

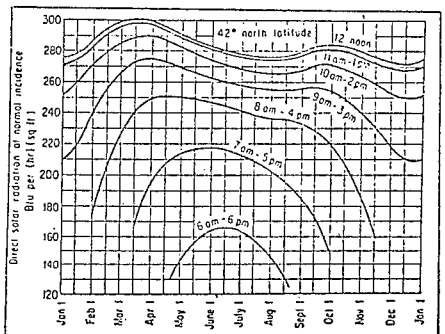

Figure 14.14 Intensity of direct solar radiation normal to the sun's rays at 42 degrees north latitude for an atmospheric clearness number of unity. (Reprinted by permission from *ASHAE Trans.*, Vol. 64, p. 64.)

CHART C—COMPARISON OF SPARK AND FIRESIDE CUSHION

| Cultivar | Inflorescence form and type | Inflorescence color | Branching pattern | Inflorescence permanence | Flowering response | Pollen |
|---|---|---|---|---|---|---|
| Spark | Flat daisy | Red | Semi-spreading | 14–18 days | 7 weeks | Scant. |
| Fireside cushion | do | Red | Semi-upright | 4–5 days | do | Abundant. |

NOTE.—Comparisons made of flowered, pinched plants grown in a greenhouse in Barberton, Ohio under conditions as described in Chart A and Chart B.

We claim:

1. A new and distinct cultivar of chrysanthemum known by the cultivar name Spark and particularly characterized as to uniqueness by the combined characteristics of flat inflorescence form; daisy inflorescence type having a slight elongation of the disc florets thereby producing a crested anemone appearance; red ray floret color; semi-spreading branching pattern; seven week flowering response; medium plant height, scant pollen; permanence of inflorescence, averaging from 14 to 18 days, and dark green foliage color with high gloss appearance.

No references cited.

ROBERT E. BAGWILL, Primary Examiner